(12) United States Patent
Fiedler et al.

(10) Patent No.: US 12,286,458 B2
(45) Date of Patent: Apr. 29, 2025

(54) BINDING PROTEINS FOR THE ENZYME ACID ALPHA GLUCOSIDASE (GAA) AND USES THEREOF

(71) Applicant: Navigo Proteins GmbH, Halle/Saale (DE)

(72) Inventors: Erik Fiedler, Halle/Saale (DE); Mathias Kahl, Halle/Saale (DE); Jonathan Lotze, Halle/Saale (DE); Eva Bosse-Doenecke, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 508 days.

(21) Appl. No.: 17/786,885

(22) PCT Filed: Dec. 17, 2020

(86) PCT No.: PCT/EP2020/086701
§ 371 (c)(1),
(2) Date: Jun. 17, 2022

(87) PCT Pub. No.: WO2021/122943
PCT Pub. Date: Jun. 24, 2021

(65) Prior Publication Data
US 2023/0027132 A1 Jan. 26, 2023

(30) Foreign Application Priority Data
Dec. 17, 2019 (EP) .................... 19217092

(51) Int. Cl.
| | |
|---|---|
| *C12N 15/09* | (2006.01) |
| *C07K 1/22* | (2006.01) |
| *C07K 14/31* | (2006.01) |
| *C12N 9/24* | (2006.01) |
| *C12N 15/10* | (2006.01) |
| *C12N 15/52* | (2006.01) |
| *G01N 33/573* | (2006.01) |

(52) U.S. Cl.
CPC ............ *C07K 14/31* (2013.01); *C12N 9/2402* (2013.01); *C12Y 302/0102* (2013.01); *G01N 33/573* (2013.01); *C07K 2319/00* (2013.01); *G01N 2333/928* (2013.01)

(58) Field of Classification Search
CPC .... C07K 1/22; C07K 2319/00; C12N 9/2402; C12N 15/09; C12N 15/101; C12N 15/52; C12Y 302/0102; G01N 2333/928; G01N 33/573
See application file for complete search history.

(56) References Cited

FOREIGN PATENT DOCUMENTS

| WO | WO 2018/029157 A1 | 2/2018 |
|---|---|---|
| WO | WO 2019/173293 A1 | 9/2019 |

OTHER PUBLICATIONS

International Search Report corresponding to International Application No. PCT/EP2020/086701 dated Mar. 3, 2021.
Written Opinion corresponding to International Application No. PCT/EP2020/086701 dated Mar. 3, 2021.

*Primary Examiner* — Maryam Monshipouri
(74) *Attorney, Agent, or Firm* — Jenkins, Taylor & Hunt, P.A.

(57) ABSTRACT

The present invention relates to the field of protein purification and relates in particular to novel proteins that bind specifically to acid alpha glucosidase (GAA). The invention further relates to fusion proteins comprising novel proteins that bind specifically to GAA. In addition, the invention relates to affinity matrices comprising the GAA binding proteins of the invention. The invention also relates to a use of these GAA binding proteins or affinity matrices for affinity purification of GAA and to methods of affinity purification of GAA using the GAA binding proteins of the invention. Further uses relate to analytical methods for the determination of GAA in liquids.

15 Claims, 2 Drawing Sheets
Specification includes a Sequence Listing.

FIGURE 1. Amino acid sequences of GAA binding proteins

| SEQ ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1 | I | A | A | K | F | D | M | K | Q | A | W | A | D | H | F | I | L | E | L | P | N | L | T | E | E | Q | R | N | A | F | R | Q | S | L | S | D | D | P | S | V | S | D | L | V | L | L | Q | A | Q | K | L | N | Q | M | Q | A | P | K |
| 2 | I | A | A | K | F | D | M | K | Q | A | W | A | D | H | F | I | L | E | L | P | N | L | T | E | E | Q | R | N | A | F | R | Q | S | L | S | D | D | P | S | V | S | D | L | V | L | A | Q | A | Q | K | L | N | Q | S | Q | A | P | K |
| 16 |   | A | K | F | D | M | K | Q | A | W | A | D | H | F | I | L | E | L | P | N | L | T | E | E | Q | R | N | A | F | R | Q | S | L | S | D | D | P | S | V | S | D | L | V | L | L | Q | A | Q | K | L | N | Q | M | Q | A | P | K |
| 17 |   | A | K | F | D | M | K | Q | A | W | A | D | H | F | I | L | E | L | P | N | L | T | E | E | Q | R | N | A | F | R | Q | S | L | S | D | D | P | S | V | S | D | L | V | L | A | Q | A | Q | K | L | N | Q | S | Q | A | P | K |
| 18 |   |   |   |   |   |   |   |   | Q | A | W | A | D | H | F | I | L | E | L | P | N | L | T | E | E | Q | R | N | A | F | R | Q | S | L | S | D | D | P | S | V | S | D | L | V | L | X | Q | A | Q | K | L | N | Q | X |   |   |   |   |

FIGURE 2. Cycle studies of GAA binding protein on Purolite Praesto 85 epoxy resin

FIGURE 2A: DBC10% of GAA binding protein

FIGURE 2B: Capacity of GAA binding protein remains about 90% after 50 x loading, elution and 0.1 M NaOH regeneration cycles

BINDING PROTEINS FOR THE ENZYME ACID ALPHA GLUCOSIDASE (GAA) AND USES THEREOF

TECHNICAL FIELD

The present invention relates to the field of protein purification and relates in particular to novel proteins that bind specifically to acid alpha glucosidase (GAA). The invention further relates to fusion proteins comprising novel proteins that bind specifically to GAA. In addition, the invention relates to affinity matrices comprising the GAA binding proteins of the invention. The invention also relates to a use of these GAA binding proteins or affinity matrices for affinity purification of GAA and to methods of affinity purification of GAA using the GAA binding proteins of the invention. Further uses relate to analytical methods for the determination of GAA in liquids.

BACKGROUND OF THE INVENTION

The lysosomal enzyme GAA (GAA) is essential in the degradation of glycogen to glucose. Defects in GAA result in the accumulation of glycogen in the lysosome and lead to muscle and nerve cell damage known as glycogen storage disease II (Pompe's disease). A therapy of this metabolic disease is the replacement of GAA. Therefore, it is essential to provide methods for the purification of the enzyme. There is an ongoing need in the art for advanced tools that allow an efficient GAA protein purification.

The present invention meets this need by providing novel GAA binding polypeptides. These novel GAA binding polypeptides are particularly advantageous as affinity ligands for GAA because they allow a precise capturing in affinity chromatography for providing highly purified GAA for medical uses.

The above overview does not necessarily describe all problems solved by the present invention.

SUMMARY OF THE INVENTION

The present disclosure provides the following items 1 to 15, without being specifically limited thereto:
1. An acid alpha glucosidase (GAA) binding protein comprising one or more GAA binding domains wherein at least one domain comprises the amino acid sequence of SEQ ID NO: 1 or of SEQ ID NO: 2 or of SEQ ID NO: 16 or of SEQ ID NO: 17 or SEQ ID NO: 18, or an amino acid sequence with at least 95% sequence identity thereto.
2. The GAA binding protein according to item 1, wherein the protein has a binding affinity of less than 200 nM for GAA (as determined by Surface Plasmon Resonance as described herein).
3. The GAA binding protein according to item 1, wherein the GAA binding protein comprises 2, 3, 4, 5, or 6 domains linked to each other.
4. The GAA binding protein according to item 3, wherein the GAA binding protein is a homo-multimer.
5. The GAA binding protein according to item 3, wherein the GAA binding protein is a hetero-multimer.
6. The GAA binding protein according to item 3, wherein one or more domains are linked to each other directly or with one or more peptide linkers.
7. A fusion protein comprising the protein according to any one of items 1-6.
8. A polynucleotide encoding the protein according to any one of items 1-6, or the fusion protein according to item 7.
9. The GAA binding protein according to any one of items 1-6, or the fusion protein according to item 7, for use in affinity purification of GAA.
10. The GAA binding protein according to any one of items 1-6, or the fusion protein according to item 7, additionally comprising one or more coupling sites for the coupling to an affinity purification matrix, preferably wherein the GAA binding protein comprises one or more Cysteine residues for the coupling to an affinity purification matrix.
11. An affinity purification matrix comprising protein according to any one of items 1-6, or the fusion protein according to item 7.
12. Use of the GAA binding protein according to any one of items 1-6, 10, or the fusion protein according to item 7, or the affinity purification matrix according to item 11 for affinity purification of GAA.
13. A method of affinity purification of GAA, the method comprising: (a) providing a liquid that contains GAA; (b) providing an affinity purification matrix comprising at least one GAA binding protein according to any one of items 1 to 6, 10, or the fusion protein according to item 7, coupled to said affinity purification matrix; (c) contacting said affinity purification matrix with the liquid under conditions that permit binding of the at least one GAA binding protein according to any one of items 1 to 6, 10, to GAA; and (d) eluting said GAA from said affinity purification matrix.
14. Use of the GAA binding protein according to items 1-6 or the fusion protein according to item 7, in methods to determine the presence of GAA.
15. A method of analyzing the presence of GAA in liquid samples, the method comprising the following steps:
    (i) providing a liquid that contains GAA,
    (ii) providing the GAA binding protein according to items 1-6, or fusion protein of item 7,
    (iii) contacting the liquid of (i) with the GAA binding protein according to items 1-6 under conditions that permit binding of the at least one GAA binding protein according to item 1 or fusion protein of item 7 to GAA,
    (iv) isolating the complex of GAA and GAA binding protein according to items 1-6 or fusion protein of item 7,
    (v) determining the amount of the GAA binding protein according to items 1-6 in the liquid of (i).

This summary of the invention is not limiting, and other aspects and embodiments of the invention will become evident from the following description, examples and drawings.

DETAILED DESCRIPTION OF THE INVENTION

The present invention provides novel polypeptides having binding affinity for GAA. The polypeptides of the present invention represent advanced and powerful tools that fill a gap in the field of protein engineering and purification. In particular, the novel polypeptides provide for an advantageous effect in protein purification by virtue of said binding affinity for GAA. Thus, the novel polypeptides of the present invention are particularly advantageous because they allow a precise capturing of GAA in affinity chromatography. The GAA binding proteins of the invention provide a highly efficient tool for the purification of GAA which might then be used for medical purposes.

The binding affinity for GAA is given by a polypeptide having SEQ ID NO: 1 or SEQ ID NO: 2 or SEQ ID NO: 16 or SEQ ID NO: 17 or SEQ ID NO: 18, or an amino acid sequence with at least 95% identity to SEQ ID NO: 1 or SEQ ID NO: 2 or SEQ ID NO: 16 or SEQ ID NO: 17 or SEQ ID NO: 18.

Before the present invention is described in more detail below it is to be understood that this invention is not limited to the particular methodology, protocols and reagents described herein as these may vary. It is also to be understood that the terminology used herein is for the purpose of describing particular aspects and embodiments only and is not intended to limit the scope of the present invention, which is reflected by the appended claims. Unless defined otherwise, all technical and scientific terms used herein have the same meaning as commonly understood by one of ordinary skill in the art to which this invention belongs. This includes a skilled person working in the field of protein engineering and purification, but also including a skilled person working in the field of developing new GAA-specific binding molecules for use in technical applications such as affinity chromatography, as well as in therapy and diagnostics.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims, which follow, unless the context requires otherwise, the word "comprise", and variants such as "comprises" and "comprising", will be understood to imply the inclusion of a stated integer or step, or group of integers or steps, but not the exclusion of any other integer or step or group of integers or steps. The term "comprise(s)" or "comprising" may encompass a limitation to "consists of" or "consisting of", should such a limitation be necessary for any reason and to any extent.

Several documents (for example: patents, patent applications, scientific publications, manufacturer's specifications, instructions, GenBank Accession Number sequence submissions etc.) may be cited throughout the present specification. Nothing herein is to be construed as an admission that the invention is not entitled to antedate such disclosure by virtue of prior invention. Some of the documents cited herein may be characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, forms part of the disclosure content of the present specification.

General Definitions of Important Terms Used in the Application

The terms "GAA binding protein" or "acid alpha glucosidase binding polypeptide" or "acid alpha glucosidase binding protein" or "GAA binding polypeptide" can be used interchangeably herein to describe a protein that is capable to bind to acid alpha glucosidase (GAA; Uniprot identifier P10253). As described herein, a "GAA binding protein" refers to a protein with detectable interaction with GAA, for example as determined by SPR analysis or other appropriate technology known to someone skilled in the art.

The terms "binding affinity" and "binding activity" may be used herein interchangeably and they refer to the ability of a polypeptide of the invention to bind to another protein, peptide, or fragment or domain thereof. Binding affinity is typically measured and reported by the equilibrium dissociation constant ($K_D$) which is used to evaluate and rank the strength of bimolecular interactions. The binding affinity and dissociation constants can be measured quantitatively. Methods for determining binding affinities are well known to the skilled person and can be selected, for instance, from the following methods that are well established in the art: surface plasmon resonance (SPR), enzyme-linked immunosorbent assay (ELISA), kinetic exclusion analysis (KinExA assay), Bio-layer interferometry (BLI), flow cytometry, fluorescence spectroscopy techniques, isothermal titration calorimetry (ITC), analytical ultracentrifugation, radioimmunoassay (RIA or IRMA), and enhanced chemiluminescence (ECL). Typically, the dissociation constant $K_D$ is determined at temperatures in the range of 20° C. and 30° C. If not specifically indicated otherwise, $K_D$ values recited herein are determined at 25° C. by SPR. The most widely used SPR-based system is the BIAcore, produced by BIAcore AB. In various embodiments of the present invention, the binding affinity for GAA may be determined by the BIAcore SPR system. In various embodiments, the concentration of the analyte is 1 µM. In various other embodiments, the concentration of the analyte is 10 µM. In various other embodiments of the present invention, the polypeptide of the invention has a binding affinity for GAA, as determined by SPR, wherein the concentration of the analyte in the SPR assay is 10 µM, preferably wherein the binding affinity is determined at 25° C.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide.

As used herein, the term "linker" refers in its broadest meaning to a molecule that covalently joins at least two other molecules.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein or polypeptide, for example, to the polypeptide of SEQ ID NO: 1. Methods for sequence alignment are well known in the art. For example, for determining the extent of an amino acid sequence identity of an arbitrary polypeptide relative to the amino acid sequence of, for example, SEQ ID NO: 1, the SIM Local similarity program is preferably employed (Xiaoquin Huang and Webb Miller (1991), Advances in Applied Mathematics, vol. 12: 337-357), that is freely available. For multiple alignment analysis, ClustalW is preferably used (Thompson et al. (1994) ucleic Acids Res., 22(22): 4673-4680).

The terms "protein" and "polypeptide" refer to any chain of two or more amino acids linked by peptide bonds and does not refer to a specific length of the product. Thus, "peptides", "protein", "amino acid chain", or any other term used to refer to a chain of two or more amino acids, are included within the definition of "polypeptide", and the term "polypeptide" may be used instead of, or interchangeably with, any of these terms. The term "polypeptide" is also intended to refer to the products of post-translational modifications of the polypeptide like, e.g., glycosylation, which are well known in the art.

The term "alkaline stable" or "alkaline stability" or "caustic stable" or "caustic stability" refers to the ability of the GAA binding protein of the invention to withstand alkaline conditions without significantly losing the ability to bind to GAA. The skilled person in this field can easily test alkaline stability by incubating a GAA binding protein with sodium hydroxide solutions, e.g., as described in the Examples, and subsequent testing of the binding activity to GAA by routine experiments known to someone skilled in the art, for example, by chromatographic approaches.

The term "chromatography" refers to separation technologies which employ a mobile phase and a stationary phase to separate one type of molecules (e.g., GAA) from other molecules (e.g., contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. GAA) in the mobile phase (the sample) i.e. the ligand has a specific binding affinity for the molecule to be purified. As understood in the context of the invention, affinity chromatography involves the addition of a sample containing an GAA to a stationary phase which comprises a chromatography ligand, such as a GAA binding protein of the invention.

The terms "solid support" or "solid matrix" are used interchangeably for the stationary phase.

The terms "affinity matrix" or "affinity purification matrix" or "affinity chromatography matrix", as used interchangeably herein, refer to a matrix, e.g., a chromatographic matrix, onto which an affinity ligand e.g., a GAA binding protein of the invention is attached. The ligand (e.g., GAA binding protein) is capable of specific binding to a molecule of interest (e.g., VH3-containing protein) which is to be purified or removed from a mixture.

The term "affinity purification" as used herein refers to a method of purifying GAA from a liquid by binding GAA to a GAA binding protein that is immobilized to a matrix. Thereby, other components of the mixture except GAA are removed. In a further step, the bound GAA can be eluted in purified form.

Detailed Description of the Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

Figure 1:
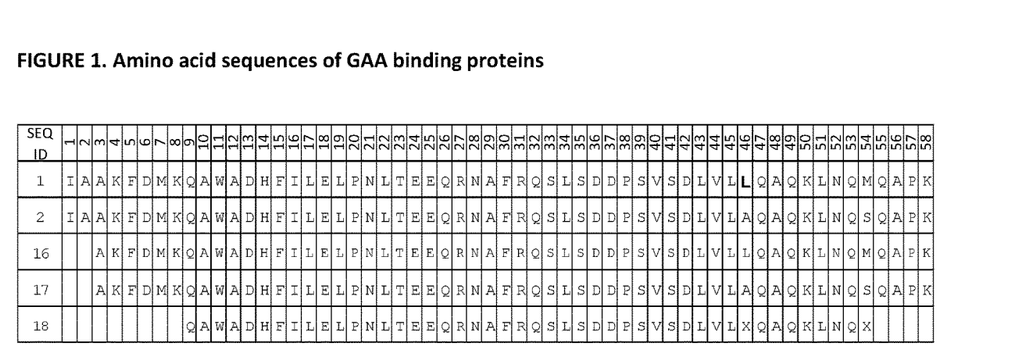
FIG. 1: shows the amino acid sequences of GAA-binding proteins.

The novel polypeptides of the present invention (including SEQ ID NOs: 1, 2, 16, 17, 18, 22, 23) exhibit a binding affinity for GAA (herein as determined by SPR). The novel binding proteins for acid alpha glucosidase comprise an amino acid sequence with at least 95% identity to any one selected from the group of SEQ ID NOs: 1-9, 14-20, 22-23. The novel GAA binding proteins are comprising one or more GAA binding domains wherein at least one GAA binding domain comprises, consists essentially of, or consists of an amino acid sequence of SEQ ID NO: 1 or SEQ ID NO: 2 or SEQ ID NO: 16 or SEQ ID NO: 17 or SEQ ID NO: 18 or an amino acid with at least 95% sequence identity thereto. The amino acid sequences of GAA binding proteins SEQ ID NO: 1 and SEQ ID NO: 2 and SEQ ID NO: 16 and SEQ ID NO: 17 and SEQ ID NO: 18 are shown in FIG. 1 and here:

```
(192403)
                                             SEQ ID NO: 1
IAAKFDMKQAWADHFILELPNLTEEQRNAFRQSLSDDPSVSDLVLLQAQKL

NQMQAPK (192402)
                                             SEQ ID NO: 2
IAAKFDMKQAWADHFILELPNLTEEQRNAFRQSLSDDPSVSDLVLAQAQKL

NQSQAPK (192403 del2N)
                                            SEQ ID NO: 16
AKFDMKQAWADHFILELPNLTEEQRNAFRQSLSDDPSVSDLVLLQAQKLNQ

MQAPK (192402 del2N)
                                            SEQ ID NO: 17
AKFDMKQAWADHFILELPNLTEEQRNAFRQSLSDDPSVSDLVLAQAQKLNQ

SQAPK.
```

The novel GAA binding proteins are comprising one or more GAA binding domains wherein at least one GAA binding domain comprises an amino acid sequence of SEQ ID NO: 18 or an amino acid with at least 95% sequence identity thereto:

```
QAWADHFILELPNLTEEQRNAFRQSLSDDPSVSDLVLX₁QAQKLNQX₂
```

$X_1$ can be any amino acid, in some embodiments selected from alanine (A) or leucine (L). $X_1$ is corresponding to position 46 in SEQ ID NO: 1 or SEQ ID NO: 2.

$X_2$ can be any amino acid, in some embodiments selected from serine (S) or methionine (M). $X_2$ is corresponding to position 54 in SEQ ID NO: 1 or SEQ ID NO: 2.

In some embodiments, the GAA binding polypeptide has at least 95% sequence identity to the amino sequence of SEQ ID NO: 1. In some embodiments, the GAA binding polypeptide has at least 95% sequence identity to the amino sequence of SEQ ID NO: 2. In some embodiments, the GAA binding polypeptide has at least 95% sequence identity to the amino sequence of SEQ ID NO: 16. In some embodiments, the GAA binding polypeptide has at least 95% sequence identity to the amino sequence of SEQ ID NO: 17 or SEQ ID NO: 18. In some embodiments, the GAA binding polypeptide has at least 95% sequence identity to the amino sequence of SEQ ID NO: 22 or SEQ ID NO: 23. In other embodiments, the GAA binding polypeptide has at least 95%, 98%, or 100% sequence identity to the amino sequence of SEQ ID NO: 1 or of SEQ ID NO: 2 or of SEQ ID NO: 16 or of SEQ ID NO: 17 or SEQ ID NO: 18 or SEQ ID NO: 22 or SEQ ID NO: 23. For example, "at least 95% identity to amino acid of SEQ ID NO: 1" refers to 1 or 2 substitutions compared to amino acid SEQ ID NO: 1; and at least "98% identity to amino acid of SEQ ID NO: 1" refers to 1 substitution compared to amino acid SEQ ID NO: 1. For example, SEQ ID NO: 2 and SEQ ID NO: 1 differ in two amino acids, i.e. amino acid 46 and amino acid 54, and are 96% identical. For example, SEQ ID NO: 16 and SEQ ID NO: 1 differ in two amino amino acids, i.e. amino acid 1 and amino acid 2 are deleted in SEQ ID NO: 16. For example, SEQ ID NO: 17 and SEQ ID NO: 2 differ in two amino amino acids, i.e. amino acid 1 and amino acid 2 are deleted in SEQ ID NO: 17.

One advantage of the disclosed GAA binding domains and proteins comprising said domains is the functional characteristic that they bind specifically to GAA. This is a particular advantage for a use as affinity ligands in the purification of GAA. The GAA binding protein of the invention is functionally characterized by a binding affinity of less than 200 nM for GAA. The GAA binding protein of the invention binds to GAA with a dissociation constant $K_D$ below 200 nM, preferably below 100 nM, or more preferably below 50 nM, as shown in Example 3.

Multimers. In one embodiment of the invention, the GAA binding protein comprises 1, 2, 3, 4, 5, or 6 GAA binding proteins linked to each other. In some embodiments, the GAA binding protein can be, for example, a monomer, a dimer, a trimer, a tetramer, a pentamer, or a hexamer. A preferred GAA binding protein is a monomer or a dimer. Multimers of the protein of the invention are fusion proteins generated artificially, generally by recombinant DNA technology well-known to a skilled person. In some embodiments, the multimer is a homo-multimer, e.g. the amino acid sequences of GAA binding proteins are identical, e.g. as shown in SEQ ID NO: 7 (dimer of SEQ ID NO: 1). In other embodiments, the multimer is a hetero-multimer, e.g. the amino acid sequences of GAA binding proteins are different.

Fusion proteins. According to one embodiment, provided herein is a fusion protein comprising one or more, for example two, GAA binding polypeptide(s) as disclosed throughout the present specification. More specifically, the fusion protein comprises one or more GAA binding polypeptide(s) as disclosed herein and a further polypeptide distinct from the polypeptide as disclosed. In various embodiments, the further polypeptide distinct from the GAA binding polypeptide as disclosed herein might be a non-Ig-binding protein, for example but not limited to, a protein that does not bind to the Fc part of immunoglobulin. In some embodiments, a non-Ig binding protein has at least 80% identity to SEQ ID NO: 10 or SEQ ID NO: 11 or SEQ ID NO: 21. In some embodiments, a non-Ig binding protein has at least 89.5% identity to SEQ ID NO: 10 or SEQ ID NO: 11 or SEQ ID NO: 21. An exemplary non-Ig binding protein is shown in amino acid sequence of SEQ ID NO: 10 or SEQ ID NO: 11 or SEQ ID NO: 21. Accordingly, some embodiments encompass fusion proteins comprising one or two GAA binding polypeptide(s) as disclosed herein and one or two non-Ig-binding polypeptide(s).

In some embodiments, a fusion protein may comprise the following combinations (from N-terminus to C-terminus):
(a) GAA binding protein—non-Ig binding protein;
(b) Non-Ig binding protein—GAA binding protein;
(c) Non-Ig binding protein—GAA binding protein—non-Ig binding protein (for example, see SEQ ID NO: 9);
(d) GAA binding protein—non-Ig binding protein—non-Ig binding protein (for example, see SEQ ID NO: 14, SEQ ID NO: 19, SEQ ID NO: 20).
(e) GAA binding protein—GAA binding protein—non-Ig binding protein-non-Ig binding protein (for example, see SEQ ID NO: 15);
(f) Non-Ig binding protein—non-Ig binding protein—GAA binding protein Other combinations of non-Ig binding protein and GAA binding protein domains are also feasible to someone skilled in the art.

In some embodiments, a fusion protein comprises a GAA binding protein of SEQ ID NO: 1, or a GAA binding protein with at least 95% amino acid identity thereto. In some embodiments, the fusion protein comprises a GAA binding protein of SEQ ID NO: 1, or a GAA binding protein with at least 95% amino acid identity thereto. In some embodiments, the fusion protein comprises a GAA binding protein of SEQ ID NO: 2, or a GAA binding protein with at least 95% amino acid identity thereto. In some embodiments, the fusion protein comprises a GAA binding protein of SEQ ID NO: 16, or a GAA binding protein with at least 95% amino acid identity thereto. In some embodiments, the fusion protein comprises a GAA binding protein of SEQ ID NO: 17, or a GAA binding protein with at least 95% amino acid identity thereto. In some embodiments, the fusion protein comprises a GAA binding protein of SEQ ID NO: 18, or a GAA binding protein with at least 95% amino acid identity thereto. In some embodiments, the fusion protein comprises a GAA binding protein of SEQ ID NO: 22 or SEQ ID NO: 23, or a GAA binding protein with at least 95% amino acid identity thereto. In some preferred embodiments, the fusion protein comprises the GAA binding protein of SEQ ID NO: 1. In other preferred embodiments, the fusion protein comprises the GAA binding protein of SEQ ID NO: 2. In other preferred embodiments, the fusion protein comprises the GAA binding protein of SEQ ID NO: 16. In other preferred embodiments, the fusion protein comprises the GAA binding protein of SEQ ID NO: 17. In other preferred embodiments, the fusion protein comprises the GAA binding protein of SEQ ID NO: 18.

The moieties of the fusion protein may be linked to each other directly head-to-tail or may be linked by a linker, wherein the linker preferably is a peptide linker. In various embodiments, a peptide linker may be considered as an amino acid sequence which sterically separates the two portions of the fusion protein. Typically, such linker consists of between 1 and 10 amino acids.

A fusion protein may be characterized as a protein formed by genetically fusing or combining a gene encoding the GAA binding polypeptide of the invention with a gene encoding a polypeptide distinct from the polypeptide as described herein above. Accordingly, the fusion protein may be considered as the product of two or more genes that were translated together (no stop-codon in between).

Molecules for purification or detection. In some embodiments, the GAA binding proteins or fusion proteins comprising the GAA binding protein may also comprise additional amino acid residues at the N-terminal end and/or at the C-terminal end, such as for example an additional sequence at the N-terminal end and/or C-terminal end. Additional sequences may include for example sequences introduced e.g. for purification or detection. Typical examples for such sequences include, without being limiting, Strep-tags (see e.g. SEQ ID NO: 12), oligohistidine-tags, glutathione S-transferase, maltose-binding protein, inteins, intein fragments, or the albumin-binding domain of protein G, or others. In one embodiment, additional amino acid sequences include one or more peptide sequences that confer an affinity to certain chromatography column materials. The GAA binding protein or fusion protein comprising an GAA binding protein may include specific attachment sites for the attachment to solid supports, preferably at the C-terminal end, such as cysteine or lysine. Examples for GAA binding proteins with C-terminal Cysteine are shown in SEQ ID NOs: 3, 4, 5, 6, 8. Examples for a GAA binding protein of the invention having N-terminal additional amino acids are shown in SEQ ID NO: 5 and SEQ ID NO: 6.

Method of generation the GAA binding protein. The present invention further provides a method for the generation of a novel GAA binding polypeptide as disclosed herein with binding affinity for GAA, the method comprising the following steps: (i) providing a population of polypeptides; (ii) contacting the population of polypeptides of (i) with GAA; (iii) identifying a complex comprising a GAA binding polypeptide bound to GAA; and (iv) obtaining a GAA binding polypeptide which is capable of binding to GAA.

The method for the generation of a novel GAA binding polypeptide with binding affinity for GAA may comprise, a further step of determining the binding affinity of the polypeptide to GAA. The binding affinity may be determined as described elsewhere herein.

Use of the novel GAA binding polypeptides in technical applications. Also provided herein is the use of any novel GAA binding polypeptide of the present invention, including fusion proteins, in technical applications, preferably for use as affinity ligands in affinity chromatography.

As described herein, affinity chromatography (also called affinity purification) makes use of specific binding interactions between molecules. Methods for immobilization of protein and methods for affinity chromatography are well-known in the field of protein purification and can be easily performed by a skilled person in this field using standard techniques and equipment.

In various embodiments, the method of affinity purification may further comprise one or more washing steps carried out under conditions sufficient to remove from the affinity purification matrix some or all molecules that are non-specifically bound thereto. Affinity purification matrices suitable for the disclosed uses and methods are known to a person skilled in the art.

Conjugation to a solid support. In various aspects and/or embodiments of the present invention, the novel polypeptides disclosed herein including novel polypeptides generated or obtained by any of the methods as described above are conjugated to a solid support. In some embodiments of the invention, the polypeptide comprises an attachment site for site-specific covalent coupling of the polypeptide to a solid support. Specific attachment sites comprise without being limited thereto, natural amino acids, such as cysteine or lysine, which enable specific chemical reactions with a reactive group of the solid phase, or a linker between the solid phase and the protein.

Affinity purification matrix. In another embodiment, an affinity purification matrix is provided comprising a GAA binding polypeptide, including a polypeptide identified by any of the methods as described above.

In preferred embodiments, the affinity purification matrix is a solid support. The affinity purification matrix comprises at least one GAA binding polypeptide provided by the present invention. Accordingly, a novel GAA binding protein disclosed herein is encompassed for use in the purification of GAA by an affinity matrix.

Solid support matrices for affinity chromatography are known in the art and include, e.g., without being limited thereto, agarose and stabilized derivatives of agarose, cellulose or derivatives of cellulose, controlled pore glass, monolith, silica, zirconium oxide, titanium oxide, or synthetic polymers, and hydrogels of various compositions and combinations of the above.

The formats for solid support matrices can be of any suitable well-known kind. Such solid support matrix for coupling a novel protein or polypeptide of the present invention might comprise, e.g., one of the following, without being limited thereto: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads. Matrices in particle form can be used as a packed bed or in a suspended form including expanded beds. In other embodiments of the invention, the solid support matrix is a membrane, for example a hydrogel membrane. In some embodiments, the affinity purification may involve a membrane as a matrix to which a GAA binding protein of the present invention is covalently bound. The solid support can also be in the form of a membrane in a cartridge.

In some embodiments, the affinity purification involves a chromatography column containing a solid support matrix to which a novel protein of the present invention is covalently bound. A novel protein or polypeptide of the present invention may be attached to a suitable solid support matrix via conventional coupling techniques. Methods for immobilization of protein ligands to solid supports are well-known in the field of protein engineering and purification and can easily be performed by a skilled person in this field using standard techniques and equipment.

Method of manufacturing GAA. Further embodiments relate to a process of manufacturing GAA thereof or a protein comprising GAA comprising at least one chromatographic step employing an affinity chromatography matrix having an affinity for specifically binding GAA protein wherein the affinity ligand (binding protein) for GAA as described above is coupled to said affinity chromatography matrix.

Method of determination of presence of GAA. Further, in some embodiments, the GAA binding protein as described herein or the fusion protein as described herein are used in methods to determine the presence of GAA. Some embodiments relate to a method of analyzing the presence of GAA in liquid samples, the method comprising the following steps: (a) providing a liquid that contains GAA, (b) providing the GAA binding protein (or fusion protein), (c) contacting the liquid that contains GAA with the GAA binding protein as described herein (or fusion protein) under conditions that permit binding of the at least one GAA binding protein (or fusion protein) to GAA, (d) isolating the complex of GAA and GAA binding protein (or fusion protein), and (e) determining the amount of the GAA binding protein (or fusion protein) which indicates the amount of GAA in the liquid of (a).

Method of quantification of GAA. Further embodiments relate to a method of quantification of GAA, the method comprising: (a) providing a liquid that contains GAA; (b) providing a matrix to which GAA binding protein as described herein (or a fusion protein) has been covalently coupled; (c) contacting said affinity purification matrix with the liquid under conditions that permit binding of the at least one GAA binding protein (or fusion protein) to GAA; (d) eluting said GAA; and optionally, (e) quantitating the amount of eluted GAA. Methods to determine the presence of GAA in liquid samples might be quantitative or qualitative. Such methods are well known to the skilled person and can be selected, for instance but limited to, from the following methods that are well established in the art: enzyme-linked immunosorbent assay (ELISA), enzymatic reactions, surface plasmon resonance (SPR) or chromatography.

Polynucleotides, vectors, host cells. One embodiment covers an (isolated) polynucleotide or nucleic acid molecule encoding a GAA binding polypeptide as disclosed herein. A further embodiment also encompasses polypeptides encoded by the polynucleotides as disclosed herein. Further provided is a vector, in particular an expression vector, comprising the isolated polynucleotide or nucleic acid molecule of the invention, as well as a host cell comprising the isolated polynucleotide or the expression vector. For example, one or more polynucleotides, which encode a polypeptide as disclosed herein may be expressed in a suitable host and the produced protein can be isolated. A vector means any molecule or entity (e.g., nucleic acid, plasmid, bacteriophage or virus) that can be used for transfer of protein-encoding information into a host cell. Suitable vectors that may be applied in the present invention are known in the art. Furthermore, an isolated cell comprising a polynucleotide or nucleic acid or a vector as disclosed herein is provided. Suitable host cells include prokaryotes or eukaryotes, for example a bacterial host cell, a yeast host cell or a non-human host cell carrying a vector. Suitable bacterial expression host cells or systems are known in the art. Various mammalian or insect cell culture systems as known in the art can also be employed to express recombinant proteins.

Method of producing a protein of the invention. In a further embodiment, a method for the production of the GAA binding polypeptide as described is provided, the method comprising the step(s): (a) culturing a (suitable) host cell under conditions suitable for the expression of a GAA binding polypeptide so as to obtain said GAA binding polypeptide; and (b) optionally isolating said GAA binding polypeptide. Suitable conditions for culturing a prokaryotic or eukaryotic host are well known to a person skilled in the art.

A GAA binding polypeptide may be prepared by any conventional and well-known techniques such as plain organic synthetic strategies, solid phase-assisted synthesis techniques, or by commercially available automated synthesizers. They may also be prepared by conventional recombinant techniques, alone or in combination with conventional synthetic techniques.

In one embodiment, a method for the preparation of GAA binding protein is provided, as detailed above, said method comprising the steps: (a) providing a nucleic acid molecule encoding a GAA binding polypeptide; (b) introducing said nucleic acid molecule into an expression vector; (c) introducing said expression vector into a host cell; (d) culturing the host cell in a culture medium; (e) subjecting the host cell to culturing conditions suitable for expression of the GAA binding polypeptide, thereby producing a GAA binding polypeptide; optionally (f) isolating the protein or polypeptide produced in step (e); and (g) optionally conjugating the protein or polypeptide to a solid matrix as described above. In various embodiments of the present invention the production of the GAA binding polypeptide is performed by cell-free in vitro transcription and translation.

The following Examples are provided for further illustration of the invention. The invention, however, is not limited thereto, and the following Examples merely show the practicability of the invention on the basis of the above description.

EXAMPLES

The following Examples are provided for further illustration of the invention. The invention, however, is not limited thereto, and the following Examples merely show the practicability of the invention on the basis of the above description. For a complete disclosure of the invention reference is made also to the literature cited in the application which is incorporated completely into the application by reference.

Example 1. Selection of GAA Binding Protein of the Invention

Library construction and cloning of libraries. A library based on a stable non-Immunoglobulin binding protein with Protein A-like structure as shown in SEQ ID NO: 10 comprising randomized amino acid positions were synthesized in house by randomized oligonucleotides generated by synthetic trinucleotide phosphoramidites (ELLA Biotech) to achieve a well-balanced amino acid distribution with simultaneously exclusion of cysteine and other amino acid residues at randomized positions. SEQ ID NO: 10 was randomized at least in amino acid positions 7, 8, 10, 11, 14, 15, 18, 20, 42, 43, 46, 47, 49, 50, 53 and 54

The corresponding cDNA library was amplified by PCR and ligated with a pCD33-OmpA phagemid. Aliquots of the ligation mixture were used for electroporation of E. coli ER2738 (Lucigen). Unless otherwise indicated, established recombinant genetic methods were used.

Primary selection by TAT Phage Display. The naive library was enriched against the biotinylated GAA (also known as Myozyme or alglucosidase alfa; Lumizyme®) using phage display as selection system. After transformation of competent bacterial ER2738 cells (Lucigene) with phagemid pCD33-OmpA carrying the library, phage amplification and purification was carried out using standard methods known to a skilled person. The selection in solution (SIS) method was utilized to allow binding between biotinylated GAA and the phage library in solution. The GAA-phage complexes were captured by streptavidin/neutravidin magnetic beads. The GAA concentration during phage incubation was lowered from 200 nM (first round) to 100 nM (second round) to 50 nM (third round), and 25 nM (fourth round). A preselection with empty magnetic beads were performed in each round. After each selection round GAA bound phages were eluted by trypsin. To identify target specific phage pools, eluted and reamplified phages of each selection round were analyzed by phage pool ELISA. Wells of a medium binding microtiter plate (Greiner Bio-One) were precoated with streptavidin (10 µg/ml) followed by coating with biotinylated GAA (2.5 μg/ml). Bound phages were detected using α-M13 HRPconjugated antibody (GE Healthcare).

Cloning of target binding phage pools into an expression vector. Selection pools showing specific binding to GAA in phage pool ELISA were amplified by PCR according to methods known in the art, cut with appropriate restriction nucleases and ligated into a derivative of the expression vector pET-28a (Merck, Germany) comprising a 10 amino acid linker consisting of proline, serine, and alanine and a sfGFP.

Example 2. Expression and Purification of GAA Binding Proteins

Hits as identified by selection as described in Example 1 were identified after screening and proteins produced in μ-scale (Phynexus).

Constructs were expressed in *Escherichia coli* BL21 (DE3) using a low copy plasmid system under regulation of a T7 promoter. Proteins were produced in soluble form after induction by lactose included in the medium (autoinduction medium). BL21 (DE3) competent cells were transformed with the expression plasmid, spread onto selective agar plates (kanamycin) and incubated overnight at 37° C. Precultures were inoculated from single colony in 3 ml 2×YT medium supplemented with 50 μg/ml kanamycin and cultured for 6 hours at 37° C. at 200 rpm in a conventional orbital shaker in culture tubes. Main cultures were inoculated with 3 mL of precultures in 300 ml ZYM-5052 (0.5% glycerol, 0.2% lactose, 0.05% glucose, 0.5% yeast extract, 1.0% casamino acids, 25 mM $Na_2HPO_4$, 25 mM $KH_2PO_4$, 5 mM $Na_2SO_4$, 2 mM $MgSO_4$ and trace elements) that was supplemented with 50 μg/ml kanamycin in 1 L Erlenmeyer flasks. Cultures were transferred to an orbital shaker and incubated at 30° C. and 200 rpm. Recombinant protein expression was induced by metabolizing glucose and subsequently allowing lactose to enter the cells. Cells were grown overnight for approx. 17 hours to reach a final OD600 of about 2-4. Before the harvest, the OD600 was measured, samples adjusted to 0.6/OD600 were withdrawn, pelleted and frozen at −20° C. To collect biomass cells were centrifuged at 12000×g for 15 min at 22° C. Pellets were weighed (wet weight). Cells were stored at −20° C. before processing.

Proteins with affinity tag were purified by affinity chromatography and size exclusion. After affinity chromatography purification a size exclusion chromatography (SE HPLC or SEC) has been performed using an Äkta system and a Superdex™200 HiLoad 16/600 column (GE Healthcare). The SEC column has a volume of 120 ml and was equilibrated with 2 CV. The samples were applied with a flow rate of 1 ml/min. Fraction collection starts as the signal intensity reaches 10 mAU. Following SDS-PAGE analysis positive fractions were pooled and their protein concentrations were measured. Further analysis included SDS-PAGE, SE-HPLC and RP-HPLC. Protein concentrations were determined by absorbance measurement at 280 nm using the molar absorbent coefficient. Reversed phase chromatography (RP-HPLC) has been performed using a Dionex HPLC system and a PLRP-S (5 μm, 300 Å) column (Agilent).

Fusion proteins of GAA binding protein and non-Ig binding protein (SEQ ID NOs: 14, 15, 19, 20) were purified by the following strategy: Q-Sepharose FF 275 ml (pH 6) (buffer A: 20 mM BisTris, 1 mM EDTA pH 6; buffer B: 20 mM BisTris, 1 mM EDTA, 1 M NaCL pH 6), Phenyl Sepharose HP 236 ml (buffer A: 20 mM BisTris, 1 mM EDTA, 1 M $(NH_4)_2SO_4$ pH 6; buffer B: 20 mM BisTris, 1 mM EDTA, pH 6), Desalting 560 ml. For example, SEQ ID NO: 14 (CID204870) was successfully purified with yield of 1 g protein per liter cell culture volume. SEQ ID NO: 19 was successfully purified with yield of 10 g protein per liter cell culture volume.

Example 3. Analysis of Proteins by Surface Plasmon Resonance (SPR)

500-1500 RU GAA (ON-ligand) was immobilized on a CM-5 sensor chip (GE Healthcare); the chip was equilibrated with SPR running buffer. GAA was biotinylated with Sulfo-NHS-Biotin standard reagent and purified via size exclusion chromatography (Superdex 200). The target protein was immobilized by injection of a biotinylated target on Streptavidin coated sensor chip. Upon ligand binding, protein analyte was accumulated on the surface increasing the refractive index. This change in the refractive index was measured in real time and plotted as response or resonance units versus time. The analytes were applied to the chip in serial dilutions with a flow rate of 30 μl/min. The association was performed for 120 seconds and the dissociation for 360 seconds. After each run, the chip surface was regenerated with 30 μl regeneration buffer (10 mM Glycine) and equilibrated with running buffer. Binding studies were carried out by the use of the BIAcore 3000 (GE Healthcare); data evaluation was operated via the BIAevaluation 3.0 software, provided by the manufacturer, by the use of the Langmuir 1:1 model (RI=0). Evaluated dissociation constants ($K_D$) were standardized against GAA and indicated. Shown is the change in refractive index measured in real time and plotted as response or resonance unit [RU] versus time [sec]. Results: The GAA binding protein as disclosed herein showed strong specific binding to immobilized GAA, with affinities of less than 100 nM (see TABLE 1). GAA binding proteins of the invention do not bind hIgG. The fusion protein of SEQ ID NO: 19 does not bind hIgG; the affinity is specific for GAA with affinities of less than 100 nM.

TABLE 1

| Specific affinity of GAA affinity ligand vs. GAA | |
| --- | --- |
| GAA affinity ligand | KD vs GAA |
| SEQ ID NO: 1 | 26.5 nM |
| SEQ ID NO: 1 (dimer) | 34 nM |
| SEQ ID NO: 1 (fusion with dimer of non-Ig binding protein)(SEQ ID NO: 14) | 55 nM |
| SEQ ID NO: 2 | 23 nM |

Example 4. The GAA Binding Protein of the Invention as Affinity Ligand for the Purification of GAA Coupling efficiency: 20 mg purified GAA binding protein (with C-terminal cysteine) was immobilized per mL Praesto™ Epoxy 85 according to the manufacturer's instructions (coupling buffer: 50 mM $Na_2HPO_4$, 150 mM NaCl, 5 mM TCEP, 2.05 M $Na_2SO_4$ (or 175 mg $Na_2SO_4$ per mL Resin), pH 9.5, coupling conditions: at 35° C. for 3 h). Results are shown in TABLE 2.

TABLE 2

| Coupling efficiency of GAA affinity ligand | |
| --- | --- |
| GAA affinity ligand | Coupling efficiency |
| SEQ ID NO: 1 | 17.0 mg/mL resin |
| SEQ ID NO: 1 (N-terminal cap) | 17.4 mg/mL resin |
| SEQ ID NO: 1 (dimer) | 19.0 mg/mL resin |
| SEQ ID NO: 2 | 17.4 mg/mL resin |
| SEQ ID NO: 2 (N-terminal cap) | 16.5 mg/mL resin |

DBC 10%: Running buffer: 20 mM citrate, 150 mM NaCl, 1 mM EDTA, pH 6,2. First elution buffer: 100 mM citrate buffer, 20% (v/v) hexylene glycol, pH 3.5; second elution buffer: 0.1 M citrate, pH 2.0 (determination of elution ratio). The dynamic binding capacity (DBC) was determined by the mass of injected GAA at 10% breakthrough at 6 min residence time. Results: The coupled resin showed good dynamic binding capacity (DBC10%) of affinity ligands (with c-terminal Cys):

SEQ ID NO: 1 with DBC10% of at least 27 mg/ml
SEQ ID NO: 1 dimer with DBC10% of at least 24 mg/ml
SEQ ID NO: 1 fusion protein (SEQ ID NO: 19) of at least 22.7 mg/ml
SEQ ID NO: 2 with DBC 10% of at least 16 mg/ml.

Caustic stability (cycling study). Samples coupled to Praesto™ Epoxy 85 (coupling conditions: 20 mg/ml, 3 h, 35° C., 2.05 M $Na_2SO_4$ pH 8.5) were treated with 0.1 M NaOH for at least 10 h (610 min) at RT. The overall elution ratio at pH 3.5 is 100%.

Results: The affinity ligands (coupled via with c-terminal Cys) showed good caustic stability in cycling studies:

SEQ ID NO: 1 (N-terminal extension) with 95% remaining capacity
SEQ ID NO: 1 dimer
  with 94.4% remaining capacity after 610 min (about 10 h)
  with 84.4% remaining capacity after 1515 min (25 h) (equals to 101 cycles).

Figures 2, 2A:
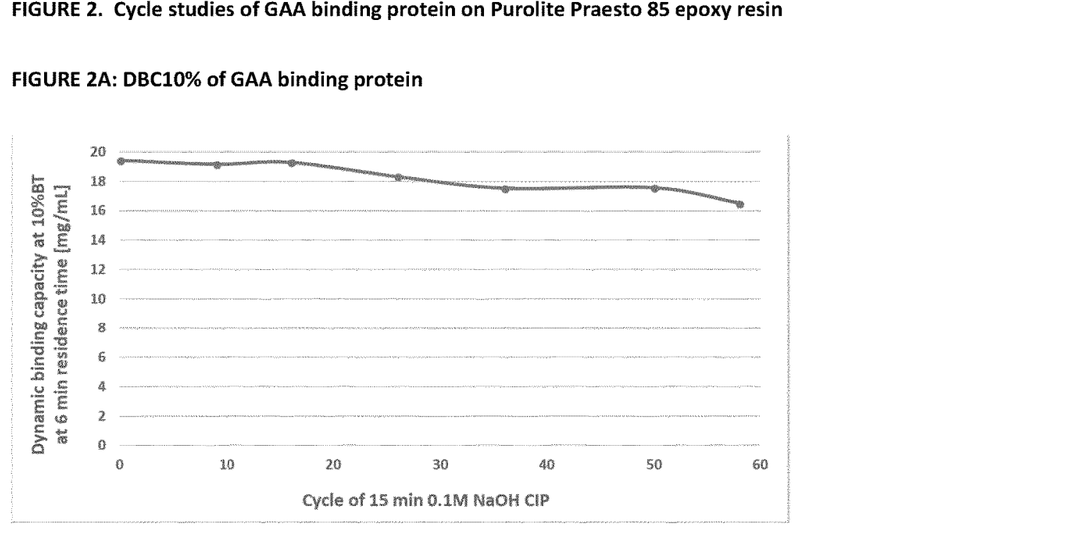
FIG. 2: shows cycle studies on Purolite Praesto 85 epoxy resin.
FIG. 2A shows the DBC10% for SED ID NO: 1 (with N-terminal extension) on Praesto 85 epoxy resin at 6 min residence time. The binding capacity was 19.5 mg/ml.
Figure 2B:
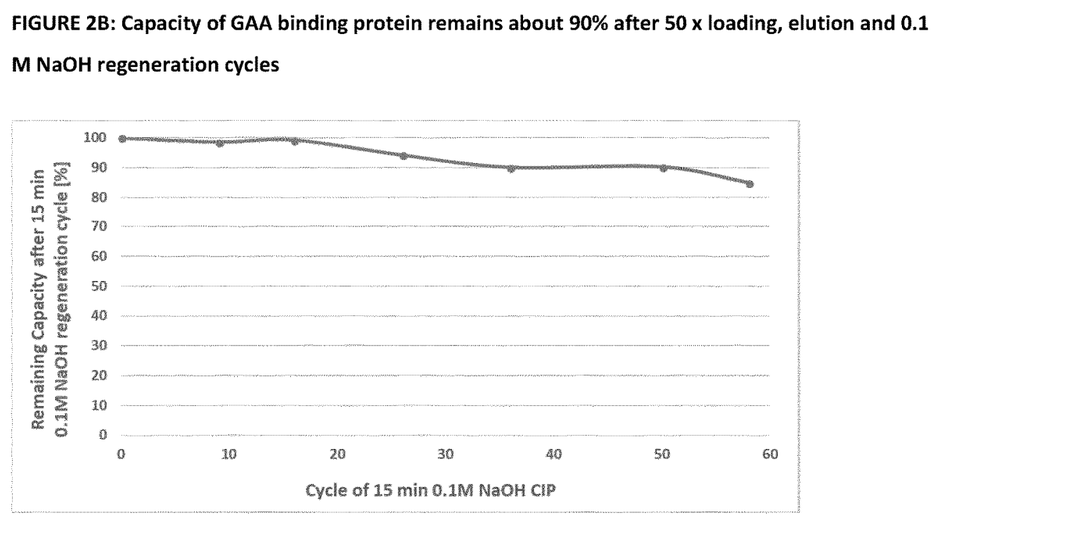
FIG. 2B shows the DBC and caustic stability of GAA-binding protein (SEQ ID NO: 1 with N-terminal extension) coupled to Praesto 85 resin and loaded with 2 mg/ml GAA. the remaining capacity after 50×loading, elution, and at 0.1 M NaOH regeneration cycles at least 90%. The DBC10% was measured at the marked dotted points on the line.

FIG. 2 shows cycling studies on Praesto™ Epoxy 85 resin. FIG. 2A shows the DBC10% for SED ID NO: 1 (with N-terminal extension) on Praesto™ Epoxy 85 at 6 min residence time. The binding capacity was 19.5 mg/ml. FIG. 2B shows the DBC10% and caustic stability of GAA-binding protein (SEQ ID NO: 1 with N-terminal extension) coupled to Praesto™ Epoxy 85 resin and loaded with 2 mg/ml GAA. The remaining capacity after 50×loading, elution, and at 0.1 M NaOH regeneration cycles was at least 90%.

TABLE 3 shows results for immobilized affinity ligands incubated in NaOH in packed column format.

TABLE 3

| | Caustic stability | |
| --- | --- | --- |
| | 192403 dimer | 192403 fusion protein |
| Structure | SEQ ID NO: 1 dimer | SEQ ID NO: 1 and two non-GAA binding stable domains with Protein A like structure (non ig binding) |
| SEQ ID NO: | 8 | 19 |
| NaOH Stability (in % remaining) | | |
| 0.1 M NaOH, 0 h | 100% | 100% |
| 0.1 M NaOH, 12.5 h | 98% | 94% |
| 0.1 M NaOH, 25 h | 92% | 87% |
| 0.1 M NaOH, 37.5 h | 85% | 80% |
| 0.1 M NaOH, 50 h | 78% | 74% |
| 0.5 M NaOH, 22 h | 79% | 77% |

The invention claimed is:

1. An acid alpha-glucosidase (GAA) binding protein comprising one or more GAA binding domains wherein at least one domain comprises the amino acid sequence of SEQ ID NO: 1 or of SEQ ID NO: 2, or an amino acid sequence with at least 95% sequence identity thereto.

2. The GAA binding protein of claim 1, wherein the protein has a binding affinity dissociation constant of less than 200 nM for GAA.

3. The GAA binding protein according to claim 1, wherein the GAA binding protein comprises 2, 3, 4, 5, or 6 domains linked to each other.

4. The GAA binding protein according to claim 3, wherein the GAA binding protein is a homo-multimer.

5. The GAA binding protein according to claim 3, wherein the GAA binding protein is a hetero-multimer.

6. The GAA binding protein according to claim 3, wherein one or more domains are linked to each other directly or with one or more peptide linkers.

7. A fusion protein comprising the GAA binding protein according to claim 1.

8. A polynucleotide encoding the GAA binding protein according to claim 1.

9. The GAA binding protein according to claim 1, further comprising one or more coupling sites for coupling the GAA binding protein to an affinity purification matrix, wherein the one or more coupling sites comprises one or more cysteine residues for coupling the GAA binding protein to an affinity purification matrix.

10. An affinity purification matrix comprising the GAA binding protein according to claim 1.

11. A method for affinity purifying GAA, the method comprising:
   (a) providing a liquid that contains GAA;
   (b) providing an affinity purification matrix comprising at least one GAA binding protein according to claim 1 coupled to said affinity purification matrix;
   (c) contacting said affinity purification matrix with the liquid under conditions that permit binding of the at least one GAA binding protein according to claim 1 to GAA; and
   (d) eluting said GAA from said affinity purification matrix, whereby GAA is affinity purified.

12. A method for determining GAA in a liquid sample, the method comprising:
   (i) providing a liquid that contains GAA,
   (ii) providing a GAA binding protein according to claim 1 or a fusion protein comprising the GAA binding protein according to claim 1,
   (iii) contacting the liquid of (i) with the GAA binding protein according to claim 1 or the fusion protein comprising the GAA binding protein according to claim 1 under conditions that permit binding of the at least one GAA binding protein according of claim 1 to GAA,
   (iv) isolating a complex of GAA and GAA binding protein according to claim 1 or the fusion protein comprising the GAA binding protein according to claim 1 formed in step (iii), wherein the GAA and the GAA binding protein/fusion protein are present in the complex in a 1:1 molar ratio, and
   (v) determining an amount of the GAA binding protein according to claim 1 or the fusion protein comprising the GAA binding protein according to claim 1 in the liquid of (i),
   (vi) whereby the GAA in the liquid sample is determined.

13. A polynucleotide encoding the fusion protein according to claim 7.

14. An affinity purification matrix comprising the fusion protein according to claim 7.

15. The fusion protein according to claim 7, further comprising one or more coupling sites for coupling the fusion protein to an affinity purification matrix, wherein one or more coupling sites comprise one or more cysteine residues for coupling the fusion protein to an affinity purification matrix.

* * * * *

SEQUENCE LISTING

```
<160> NUMBER OF SEQ ID NOS: 23

<210> SEQ ID NO 1
<211> LENGTH: 58
<212> TYPE: PRT
<213> ORGANISM: Artificial Sequence
<220> FEATURE:
<223> OTHER INFORMATION: Artificially synthesized GAA binding protein
      (monomer)

<400> SEQUENCE: 1

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
                20                  25                  30

Ser Leu Ser Asp Asp Pro Ser Val Ser Asp Leu Val Leu Leu Gln Ala
            35                  40                  45

Gln Lys Leu Asn Gln Met Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Artificially synthesized GAA binding protein
```

-continued

```
<400> SEQUENCE: 2

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
            20                  25                  30

Ser Leu Ser Asp Asp Pro Ser Val Ser Asp Leu Val Leu Ala Gln Ala
        35                  40                  45

Gln Lys Leu Asn Gln Ser Gln Ala Pro Lys
    50                  55

<210> SEQ ID NO 3
<211> LENGTH: 59
<212> TYPE: PRT
<213> ORGANISM: Artificial Sequence
<220> FEATURE:
<223> OTHER INFORMATION: Artificially synthesized GAA binding protein
      (with C-terminal Cys)

<400> SEQUENCE: 3

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
            20                  25                  30

Ser Leu Ser Asp Asp Pro Ser Val Ser Asp Leu Val Leu Leu Gln Ala
        35                  40                  45

Gln Lys Leu Asn Gln Met Gln Ala Pro Lys Cys
    50                  55

<210> SEQ ID NO 4
<211> LENGTH: 59
<212> TYPE: PRT
<213> ORGANISM: Artificial Sequence
<220> FEATURE:
<223> OTHER INFORMATION: Artificially synthesized GAA binding protein
      (C-terminal Cys)

<400> SEQUENCE: 4

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
            20                  25                  30

Ser Leu Ser Asp Asp Pro Ser Val Ser Asp Leu Val Leu Ala Gln Ala
        35                  40                  45

Gln Lys Leu Asn Gln Ser Gln Ala Pro Lys Cys
    50                  55

<210> SEQ ID NO 5
<211> LENGTH: 65
<212> TYPE: PRT
<213> ORGANISM: Artificial Sequence
<220> FEATURE:
<223> OTHER INFORMATION: Artificially synthesized GAA binding protein
      (N-cap and C-terminal Cys)

<400> SEQUENCE: 5

Val Asp Ala Lys Phe Asp Ile Ala Ala Lys Phe Asp Met Lys Gln Ala
1               5                   10                  15

Trp Ala Asp His Phe Ile Leu Glu Leu Pro Asn Leu Thr Glu Glu Gln
            20                  25                  30

Arg Asn Ala Phe Arg Gln Ser Leu Ser Asp Asp Pro Ser Val Ser Asp
```

```
                    35                  40                  45

Leu Val Leu Gln Ala Gln Lys Leu Asn Gln Met Gln Ala Pro Lys
    50                  55                  60

Cys
65

<210> SEQ ID NO 6
<211> LENGTH: 65
<212> TYPE: PRT
<213> ORGANISM: Artificial Sequence
<220> FEATURE:
<223> OTHER INFORMATION: Artificially synthesized GAA binding protein
      (N-cap and C-terminal Cys)

<400> SEQUENCE: 6

Val Asp Ala Lys Phe Asp Ile Ala Ala Lys Phe Asp Met Lys Gln Ala
1               5                   10                  15

Trp Ala Asp His Phe Ile Leu Glu Leu Pro Asn Leu Thr Glu Glu Gln
                    20                  25                  30

Arg Asn Ala Phe Arg Gln Ser Leu Ser Asp Asp Pro Ser Val Ser Asp
                35                  40                  45

Leu Val Leu Ala Gln Ala Gln Lys Leu Asn Gln Ser Gln Ala Pro Lys
    50                  55                  60

Cys
65

<210> SEQ ID NO 7
<211> LENGTH: 116
<212> TYPE: PRT
<213> ORGANISM: Artificial Sequence
<220> FEATURE:
<223> OTHER INFORMATION: Artificially synthesized GAA binding protein
      (dimer)

<400> SEQUENCE: 7

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
                    20                  25                  30

Ser Leu Ser Asp Asp Pro Ser Val Ser Asp Leu Val Leu Leu Gln Ala
                35                  40                  45

Gln Lys Leu Asn Gln Met Gln Ala Pro Lys Ile Ala Ala Lys Phe Asp
    50                  55                  60

Met Lys Gln Ala Trp Ala Asp His Phe Ile Leu Glu Leu Pro Asn Leu
65                  70                  75                  80

Thr Glu Glu Gln Arg Asn Ala Phe Arg Gln Ser Leu Ser Asp Asp Pro
                    85                  90                  95

Ser Val Ser Asp Leu Val Leu Leu Gln Ala Gln Lys Leu Asn Gln Met
                100                 105                 110

Gln Ala Pro Lys
        115

<210> SEQ ID NO 8
<211> LENGTH: 117
<212> TYPE: PRT
<213> ORGANISM: Artificial Sequence
<220> FEATURE:
<223> OTHER INFORMATION: Artificially synthesized GAA binding protein
      (dimer with C-terminal Cys)

<400> SEQUENCE: 8
```

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
            20                  25                  30

Ser Leu Ser Asp Asp Pro Ser Val Ser Asp Leu Val Leu Leu Gln Ala
            35                  40                  45

Gln Lys Leu Asn Gln Met Gln Ala Pro Lys Ile Ala Ala Lys Phe Asp
    50                  55                  60

Met Lys Gln Ala Trp Ala Asp His Phe Ile Leu Glu Leu Pro Asn Leu
65                  70                  75                  80

Thr Glu Glu Gln Arg Asn Ala Phe Arg Gln Ser Leu Ser Asp Asp Pro
                85                  90                  95

Ser Val Ser Asp Leu Val Leu Leu Gln Ala Gln Lys Leu Asn Gln Met
            100                 105                 110

Gln Ala Pro Lys Cys
            115

<210> SEQ ID NO 9
<211> LENGTH: 174
<212> TYPE: PRT
<213> ORGANISM: Artificial Sequence
<220> FEATURE:
<223> OTHER INFORMATION: Artificially synthesized Fusion protein GAA
      binding protein

<400> SEQUENCE: 9

Ile Ala Ala Lys Phe Asp Glu Ala Gln Gln Ala Asp Tyr Glu Ile
1               5                   10                  15

Leu His Leu Pro Asn Leu Thr Glu Glu Gln Arg Asn Ala Phe Arg Gln
            20                  25                  30

Ser Leu Arg Asp Asp Pro Ser Val Ser Leu Glu Val Leu Gly Glu Ala
            35                  40                  45

Gln Lys Leu Asn Asp Ser Gln Ala Pro Lys Ile Ala Ala Lys Phe Asp
    50                  55                  60

Met Lys Gln Ala Trp Ala Asp His Phe Ile Leu Glu Leu Pro Asn Leu
65                  70                  75                  80

Thr Glu Glu Gln Arg Asn Ala Phe Arg Gln Ser Leu Ser Asp Asp Pro
                85                  90                  95

Ser Val Ser Asp Leu Val Leu Leu Gln Ala Gln Lys Leu Asn Gln Met
            100                 105                 110

Gln Ala Pro Lys Ile Ala Ala Lys Phe Asp Glu Ala Gln Gln Ala Ala
            115                 120                 125

Asp Tyr Glu Ile Leu His Leu Pro Asn Leu Thr Glu Glu Gln Arg Asn
    130                 135                 140

Ala Phe Arg Gln Ser Leu Arg Asp Asp Pro Ser Val Ser Leu Glu Val
145                 150                 155                 160

Leu Gly Glu Ala Gln Lys Leu Asn Asp Ser Gln Ala Pro Lys
            165                 170

<210> SEQ ID NO 10
<211> LENGTH: 58
<212> TYPE: PRT
<213> ORGANISM: Artificial Sequence
<220> FEATURE:
<223> OTHER INFORMATION: Artificially synthesized non-Fc binding
      protein; scaffold protein

<400> SEQUENCE: 10

Ile Ala Ala Lys Phe Asp Glu Ala Gln Ser Ala Ala Asp Ser Glu Ile
1               5                   10                  15

Leu His Leu Pro Asn Leu Thr Glu Glu Gln Arg Asn Ala Phe Arg Gln
                20                  25                  30

Ser Leu Ser Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Artificially synthesized non-Fc binding protein

<400> SEQUENCE: 11

Ile Ala Ala Lys Phe Asp Glu Ala Gln Gln Ala Ala Asp Tyr Glu Ile
1               5                   10                  15

Leu His Leu Pro Asn Leu Thr Glu Glu Gln Arg Asn Ala Phe Arg Gln
                20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 12
<211> LENGTH: 10
<212> TYPE: PRT
<213> ORGANISM: Artificial Sequence
<220> FEATURE:
<223> OTHER INFORMATION: Artificially synthesized Streptag

<400> SEQUENCE: 12

Ser Ala Trp Ser His Pro Gln Phe Glu Lys
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Artificially synthesized flag-tag

<400> SEQUENCE: 13

Asp Tyr Lys Asp Asp Asp Asp Lys
1               5

<210> SEQ ID NO 14
<211> LENGTH: 174
<212> TYPE: PRT
<213> ORGANISM: Artificial Sequence
<220> FEATURE:
<223> OTHER INFORMATION: Artificially synthesized 204870 cor1-PAdelFc2-
      PAdelFc2

<400> SEQUENCE: 14

Ile Ala Ala Lys Phe Asp Met Lys Gln Ala Trp Ala Asp His Phe Ile
1               5                   10                  15

Leu Glu Leu Pro Asn Leu Thr Glu Glu Gln Arg Asn Ala Phe Arg Gln
                20                  25                  30

Ser Leu Ser Asp Asp Pro Ser Val Ser Asp Leu Val Leu Leu Gln Ala

```
                    35                  40                  45
Gln Lys Leu Asn Gln Met Gln Ala Pro Lys Ile Ala Ala Lys Phe Asp
 50                  55                  60
Glu Ala Gln Gln Ala Ala Asp Tyr Glu Ile Leu His Leu Pro Asn Leu
 65                  70                  75                  80
Thr Glu Glu Gln Arg Asn Ala Phe Arg Gln Ser Leu Arg Asp Asp Pro
                     85                  90                  95
Ser Val Ser Leu Glu Val Leu Gly Glu Ala Gln Lys Leu Asn Asp Ser
                    100                 105                 110
Gln Ala Pro Lys Ile Ala Ala Lys Phe Asp Glu Ala Gln Gln Ala Ala
                    115                 120                 125
Asp Tyr Glu Ile Leu His Leu Pro Asn Leu Thr Glu Glu Gln Arg Asn
                    130                 135                 140
Ala Phe Arg Gln Ser Leu Arg Asp Asp Pro Ser Val Ser Leu Glu Val
145                 150                 155                 160
Leu Gly Glu Ala Gln Lys Leu Asn Asp Ser Gln Ala Pro Lys
                    165                 170
```

<210> SEQ ID NO 15
<211> LENGTH: 232
<212> TYPE: PRT
<213> ORGANISM: Artificial Sequence
<220> FEATURE:
<223> OTHER INFORMATION: Artificially synthesized core1 dimer - PAdelFc2
    dimer

<400> SEQUENCE: 15

```
Ile Ala Ala Lys Phe Asp Met Lys Gln Ala Trp Ala Asp His Phe Ile
  1               5                  10                  15
Leu Glu Leu Pro Asn Leu Thr Glu Glu Gln Arg Asn Ala Phe Arg Gln
                 20                  25                  30
Ser Leu Ser Asp Asp Pro Ser Val Ser Asp Leu Val Leu Leu Gln Ala
                 35                  40                  45
Gln Lys Leu Asn Gln Met Gln Ala Pro Lys Ile Ala Ala Lys Phe Asp
 50                  55                  60
Met Lys Gln Ala Trp Ala Asp His Phe Ile Leu Glu Leu Pro Asn Leu
 65                  70                  75                  80
Thr Glu Glu Gln Arg Asn Ala Phe Arg Gln Ser Leu Ser Asp Asp Pro
                     85                  90                  95
Ser Val Ser Asp Leu Val Leu Leu Gln Ala Gln Lys Leu Asn Gln Met
                    100                 105                 110
Gln Ala Pro Lys Ile Ala Ala Lys Phe Asp Glu Ala Gln Gln Ala Ala
                    115                 120                 125
Asp Tyr Glu Ile Leu His Leu Pro Asn Leu Thr Glu Glu Gln Arg Asn
                    130                 135                 140
Ala Phe Arg Gln Ser Leu Arg Asp Asp Pro Ser Val Ser Leu Glu Val
145                 150                 155                 160
Leu Gly Glu Ala Gln Lys Leu Asn Asp Ser Gln Ala Pro Lys Ile Ala
                    165                 170                 175
Ala Lys Phe Asp Glu Ala Gln Gln Ala Ala Asp Tyr Glu Ile Leu His
                    180                 185                 190
Leu Pro Asn Leu Thr Glu Glu Gln Arg Asn Ala Phe Arg Gln Ser Leu
                    195                 200                 205
Arg Asp Asp Pro Ser Val Ser Leu Glu Val Leu Gly Glu Ala Gln Lys
                    210                 215                 220
```

Leu Asn Asp Ser Gln Ala Pro Lys
225                 230

<210> SEQ ID NO 16
<211> LENGTH: 56
<212> TYPE: PRT
<213> ORGANISM: Artificial Sequence
<220> FEATURE:
<223> OTHER INFORMATION: Artificially synthesized GAA binding protein

<400> SEQUENCE: 16

Ala Lys Phe Asp Met Lys Gln Ala Trp Ala Asp His Phe Ile Leu Glu
1               5                   10                  15

Leu Pro Asn Leu Thr Glu Glu Gln Arg Asn Ala Phe Arg Gln Ser Leu
            20                  25                  30

Ser Asp Asp Pro Ser Val Ser Asp Leu Val Leu Leu Gln Ala Gln Lys
        35                  40                  45

Leu Asn Gln Met Gln Ala Pro Lys
    50                  55

<210> SEQ ID NO 17
<211> LENGTH: 56
<212> TYPE: PRT
<213> ORGANISM: Artificial Sequence
<220> FEATURE:
<223> OTHER INFORMATION: Artificially synthesized GAA binding protein

<400> SEQUENCE: 17

Ala Lys Phe Asp Met Lys Gln Ala Trp Ala Asp His Phe Ile Leu Glu
1               5                   10                  15

Leu Pro Asn Leu Thr Glu Glu Gln Arg Asn Ala Phe Arg Gln Ser Leu
            20                  25                  30

Ser Asp Asp Pro Ser Val Ser Asp Leu Val Leu Ala Gln Ala Gln Lys
        35                  40                  45

Leu Asn Gln Ser Gln Ala Pro Lys
    50                  55

<210> SEQ ID NO 18
<211> LENGTH: 46
<212> TYPE: PRT
<213> ORGANISM: Artificial Sequence
<220> FEATURE:
<223> OTHER INFORMATION: Artificially synthesized AA binding protein
<220> FEATURE:
<221> NAME/KEY: MISC_FEATURE
<222> LOCATION: (38)..(38)
<223> OTHER INFORMATION: Xaa may be any amino acid
<220> FEATURE:
<221> NAME/KEY: MISC_FEATURE
<222> LOCATION: (46)..(46)
<223> OTHER INFORMATION: Xaa may be any amino acid

<400> SEQUENCE: 18

Gln Ala Trp Ala Asp His Phe Ile Leu Glu Leu Pro Asn Leu Thr Glu
1               5                   10                  15

Glu Gln Arg Asn Ala Phe Arg Gln Ser Leu Ser Asp Asp Pro Ser Val
            20                  25                  30

Ser Asp Leu Val Leu Xaa Gln Ala Gln Lys Leu Asn Gln Xaa
        35                  40                  45

<210> SEQ ID NO 19
<211> LENGTH: 171
<212> TYPE: PRT
<213> ORGANISM: Artificial Sequence

```
<220> FEATURE:
<223> OTHER INFORMATION: Artificially synthesized fusion protein
      comprising GAA binding protein

<400> SEQUENCE: 19

Ala Lys Phe Asp Met Lys Gln Ala Trp Ala Asp His Phe Ile Leu Glu
1               5                   10                  15

Leu Pro Asn Leu Thr Glu Glu Gln Arg Asn Ala Phe Arg Gln Ser Leu
            20                  25                  30

Ser Asp Asp Pro Ser Val Ser Asp Leu Val Leu Leu Ala Gln Ala Gln Lys
            35                  40                  45

Leu Asn Gln Met Gln Ala Pro Lys Ala Gln His Asp Lys Asp Gln Gln
        50                  55                  60

Ala Ala Asp Lys Glu Ile Leu His Leu Pro Asn Leu Thr Glu Glu Gln
65                  70                  75                  80

Arg Asn Lys Phe Arg Gln Ser Leu Arg Asp Asp Pro Ser Val Ser Ala
                85                  90                  95

Glu Ile Leu Ala Glu Ala Lys Lys Leu Asn Asp Ala Gln Ala Pro Lys
                100                 105                 110

Ile Ala Ala Gln His Asp Lys Asp Gln Gln Ala Ala Asp Lys Glu Ile
            115                 120                 125

Leu His Leu Pro Asn Leu Thr Glu Glu Gln Arg Asn Lys Phe Arg Gln
        130                 135                 140

Ser Leu Arg Asp Asp Pro Ser Val Ser Ala Glu Ile Leu Ala Glu Ala
145                 150                 155                 160

Lys Lys Leu Asn Asp Ala Gln Ala Pro Lys Cys
                165                 170

<210> SEQ ID NO 20
<211> LENGTH: 171
<212> TYPE: PRT
<213> ORGANISM: Artificial Sequence
<220> FEATURE:
<223> OTHER INFORMATION: Artificially synthesized fusion protein
      comprising GAA binding protein

<400> SEQUENCE: 20

Ala Lys Phe Asp Met Lys Gln Ala Trp Ala Asp His Phe Ile Leu Glu
1               5                   10                  15

Leu Pro Asn Leu Thr Glu Glu Gln Arg Asn Ala Phe Arg Gln Ser Leu
            20                  25                  30

Ser Asp Asp Pro Ser Val Ser Asp Leu Val Leu Ala Gln Ala Gln Lys
            35                  40                  45

Leu Asn Gln Ser Gln Ala Pro Lys Ala Gln His Asp Lys Asp Gln Gln
        50                  55                  60

Ala Ala Asp Lys Glu Ile Leu His Leu Pro Asn Leu Thr Glu Glu Gln
65                  70                  75                  80

Arg Asn Lys Phe Arg Gln Ser Leu Arg Asp Asp Pro Ser Val Ser Ala
                85                  90                  95

Glu Ile Leu Ala Glu Ala Lys Lys Leu Asn Asp Ala Gln Ala Pro Lys
                100                 105                 110

Ile Ala Ala Gln His Asp Lys Asp Gln Gln Ala Ala Asp Lys Glu Ile
            115                 120                 125

Leu His Leu Pro Asn Leu Thr Glu Glu Gln Arg Asn Lys Phe Arg Gln
        130                 135                 140

Ser Leu Arg Asp Asp Pro Ser Val Ser Ala Glu Ile Leu Ala Glu Ala
145                 150                 155                 160
```

```
Lys Lys Leu Asn Asp Ala Gln Ala Pro Lys Cys
            165                 170

<210> SEQ ID NO 21
<211> LENGTH: 58
<212> TYPE: PRT
<213> ORGANISM: Artificial Sequence
<220> FEATURE:
<223> OTHER INFORMATION: Artificially synthesized non Ig binding protein

<400> SEQUENCE: 21

Ile Ala Ala Gln His Asp Lys Ile Gln Gln Ala Ala Asp Lys Glu Ile
1               5                   10                  15

Leu His Leu Pro Asn Leu Thr Glu Glu Gln Arg Asn Lys Phe Arg Gln
            20                  25                  30

Ser Leu Arg Asp Asp Pro Ser Val Ser Ala Glu Ile Leu Ala Glu Ala
        35                  40                  45

Lys Lys Leu Asn Asp Ala Gln Ala Pro Lys
    50                  55

<210> SEQ ID NO 22
<211> LENGTH: 46
<212> TYPE: PRT
<213> ORGANISM: Artificial Sequence
<220> FEATURE:
<223> OTHER INFORMATION: Artificially synthesized GAA binding protein

<400> SEQUENCE: 22

Gln Ala Trp Ala Asp His Phe Ile Leu Glu Leu Pro Asn Leu Thr Glu
1               5                   10                  15

Glu Gln Arg Asn Ala Phe Arg Gln Ser Leu Ser Asp Asp Pro Ser Val
            20                  25                  30

Ser Asp Leu Val Leu Leu Gln Ala Gln Lys Leu Asn Gln Met
        35                  40                  45

<210> SEQ ID NO 23
<211> LENGTH: 46
<212> TYPE: PRT
<213> ORGANISM: Artificial Sequence
<220> FEATURE:
<223> OTHER INFORMATION: Artificially synthesized GAA binding protein

<400> SEQUENCE: 23

Gln Ala Trp Ala Asp His Phe Ile Leu Glu Leu Pro Asn Leu Thr Glu
1               5                   10                  15

Glu Gln Arg Asn Ala Phe Arg Gln Ser Leu Ser Asp Asp Pro Ser Val
            20                  25                  30

Ser Asp Leu Val Leu Ala Gln Ala Gln Lys Leu Asn Gln Ser
        35                  40                  45
```